United States Patent [19]

Hornstra

[11] Patent Number: 4,580,283
[45] Date of Patent: Apr. 1, 1986

[54] TWO-CRYSTAL X-RAY SPECTROMETER

[75] Inventor: Jan Hornstra, Eindhoven, Netherlands

[73] Assignee: U.S. Philips Corporation, New York, N.Y.

[21] Appl. No.: 645,882

[22] Filed: Aug. 30, 1984

[30] Foreign Application Priority Data

Sep. 14, 1983 [GB] United Kingdom ............. 8324588

[51] Int. Cl.$^4$ ............................................. G01T 1/36
[52] U.S. Cl. .......................................... 378/82; 378/85
[58] Field of Search ............................... 378/82, 84, 85

[56] References Cited

U.S. PATENT DOCUMENTS 3,639,759   2/1972   Goshi et al. ......................... 378/82

Primary Examiner—Alfred E. Smith
Assistant Examiner—Jack I. Berman
Attorney, Agent, or Firm—Paul R. Miller

[57] ABSTRACT

A two-crystal X-ray spectrometer in which hinged radius arms carry respective crystals 3, 4, at equal radii, and a spectrometer wavelength adjustment modifies the angular disposition of the source 1 and detector 5 about the corresponding crystals 3, 4, at half the hinge angle rate. Hitherto the crystals were mounted radially.

The improvement consists of displacing the crystals 3, 4, through opposite angles $\phi$ to the radius line 7', 11', where $\phi$ lies in the range 50 to 70 degrees. This enables the glancing incidence angle $\theta$ to be adjusted from 0 to 75 degrees without obstruction of the beam due to the detector 5.

To reduce the detector background due to scattered radiation, screening blades 70, 71, are moved perpendicularly to the center of the respective crystal surface just clear of the spectrometer beam. This enables the arrangement to be more compact than the prior use of Soller slits.

6 Claims, 7 Drawing Figures

$\theta = 30°$

Fig. 7.

$\theta = 60°$

TWO-CRYSTAL X-RAY SPECTROMETER

The invention relates to a two-crystal X-ray spectrometer including support means fixed relative to a source of X-radiation to be analysed, a first crystal fixedly mounted on a first member pivotable relative to said support means about a first axis through the first crystal and perpendicular to the plane of the spectrometer, a second crystal fixedly mounted on a second member pivotally carried by said first member so as to be angularly displaceable about a second axis perpendicular to the plane of the spectrometer, said first and second crystals being speced from said second axis by the same distance, detector means pivotable about a third axis through the second crystal and perpendicular to the plane of the spectrometer, the source, the first and second crystals and the detector means being arranged relative to one another such that when X-radiation corresponding to the wavelength to which the spectrometer is adjusted, is directed from the source onto the first crystal, it will be reflected in accordance with the Bragg condition for reflection onto the second crystal and, similarly, from thence onto the detector means, and means for adjusting the spectrometer wavelength comprising angular displacement means for respectively displacing the first member about the first axis and the detector means relative to the second member about the third axis, each by an angular amount $\Delta\theta$, and for displacing the second member about the second axis relative to the first member by an angular amount $2\Delta\theta$. Such an X-ray spectrometer will be referred to herein as an X-ray spectrometer of the kind specified.

It is to be understood herein that the spectrometer beam refers to that part of X-radiation from the source whose lateral extent coincides with that of radiation which is Bragg-reflected in succession by the first and second crystals onto the detector means, and the plane of the spectrometer is that plane containing the central axis of the spectrometer beam as it passed through the spectrometer, and which is at right angles to the two crystals.

Conventional X-ray spectroscopy for fluorescent X-ray analysis, normally makes use of the Bragg condition for reflection from successive planes of a crystal lattice, given by the formula:

$$2d \sin\theta = n\lambda,$$

where $\theta$ is the glancing angle, i.e. the angle between both the incident and the reflected X-ray beam and the lattice planes in question, d is the spacing between the lattice planes, $\lambda$ is the wavelength of the reflected X-radiation in the same units as d, and n is an integer.

A commonly used X-ray spectrometer arrangement is the two-crystal spectrometer in which a beam of X-rays to be analysed is directed onto a first crystal from which it is reflected onto a second crystal and thence by reflection onto a detector. Reflection at both crystals takes place according to the Bragg condition for a given wavelength $\lambda$ to which the glancing angle $\theta$ for each crystal is set by the spectrometer. The two crystals are identical, highly uniform, single crystals, each with its major surfaces parallel to the lattice plane to be used for reflection, and examples of such crystals are mono-crystals of germanium or silicon, although other crystals can be used for other wavelength ranges, such as lithium fluoride, penta erithritol or thallium acid phthalate (TAP).

In order to scan a spectral region, the orientation of each crystal must be very accurately controlled so that the angle of incidence on the second crystal is maintained the same as the angle of reflection from the first crystal, as the value of $\theta$ and therefore of $\lambda$ is adjusted. In addition, the second crystal and the detector have to be made to follow the beams reflected from the first and second crystal, respectively.

In order to simplify the mechanical problems of accurately adjusting the two crystals in step with one another, a spectrometer of the kind specified in the opening paragraph, has been proposed in a paper by Yohichi Gohshi et al. in Spectrochimica Acta, 27B (1972) pp. 135–142, and further disclosed in U.S. Pat. No. 3,639,759. In the spectrometer therein described, the first and second members to which the respective crystals are fixedly attached, are mutually pivoted about the second axis forming a kind of hinged arrangement, and each crystal is mounted so as to lie in or parallel to a respective radial plane which also includes the second axis. The advantage of the arrangement is that the critical adjustment of the relative orientation of the two crystals, which primarily determines the spectrometer wavelength, is effected by the said relative angular displacement about the second axis, and only that displacement requires to be of the highest accuracy. A disadvantage of the arrangement disclosed is that owing to the necessity for the detector to follow the reflected beam from the second crystal, only a restricted range of values for the glancing angle $\theta$ can be attained and the ray path also has to be rather long in order to make room for the Soller slits employed to prevent scattered radiation from reaching the detector. This situation is made even more difficult when an attempt is made to employ the larger crystals now available as a result of improvements in manufacture.

It is an object of the invention to provide an improved X-ray spectrometer of the kind specified in which the angle of incidence can be varied throughout a wide and useful range, and in which the background intensity can be significantly reduced.

According to the invention there is provided a two-crystal X-ray spectrometer of the kind specified, characterised in that each crystal is mounted on the corresponding first and second member so as to be respectively inclined in opposite directions through the same predetermined angle $\Phi$ to the direction joining the centre of the crystal to the second angle, wherein the value of $\Phi$ lies in the range from 50 to 70 degrees.

The invention is based on the realisation that in a two-crystal X-ray spectrometer of the kind specified, the range of the glancing angle $\theta$ can be usefully extended by inclining each of the two crystals in opposite directions relative to the respective radii from the second axis so as to lie in the specified range, and that it is also possible by this means to use large crystals up to about 5 cms across enabling the detected intensity to be increased without the need materially to increase the size of the spectrometer.

In an embodiment, first and second screening blades are provided each arranged to be respectively displaceable perpendicular to the associated reflection plane of the corresponding first and second crystal along a path which passes through the corresponding first or third axis, the blades being displaced in response to adjustment of the spectrometer wavelength so that the edge of the blade is maintained just clear of the spectrometer beam path.

This arrangement of screening blades can provide a compact and efficient screening arrangement which can significantly reduce the unwanted background due to scattered radiation otherwise to be found in the detector output signal.

An embodiment of the invention will now be described by way of example, with reference to the accompanying drawings, of which.

Figure 1:
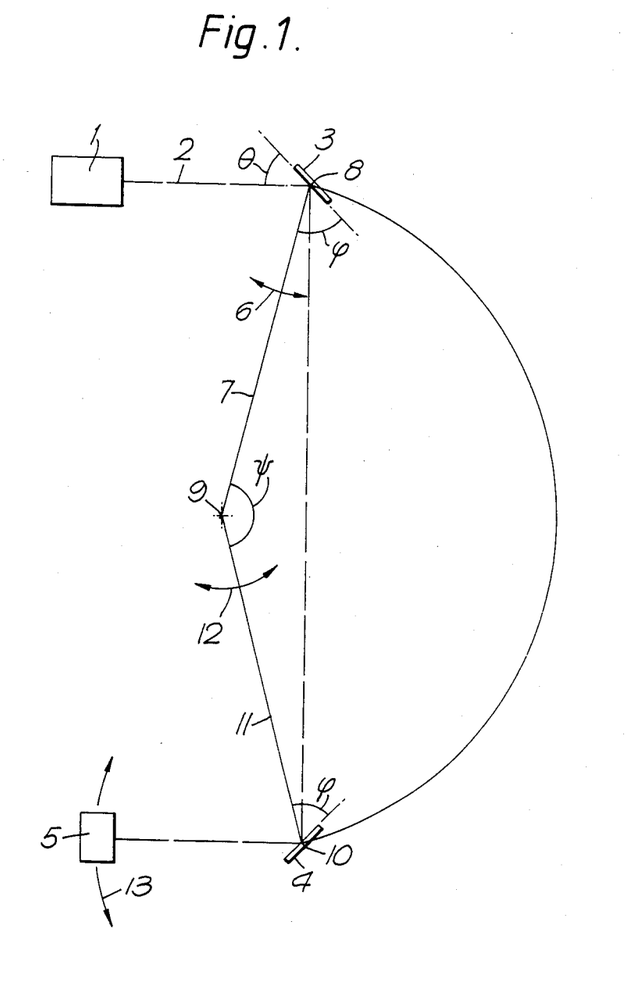
FIG. 1 is a schematic diagram illustrating the principles of apparatus in accordance with the invention.

The principle of a two-crystal X-ray spectrometer in accordance with the invention will first be explained with reference to FIGS. 1 and 2. FIG. 1 illustrates a spectrometer wavelength adjustment near the centre of the range of adjustment in which a source 1 of X-radiation to be analysed directs a beam of radiation 2 at a first crystal 3 at a glancing angle $\theta = 45°$. Radiation of wavelength $\lambda$ for which the aforementioned Bragg condition of reflection is satisfied, namely:

$$2d \sin \theta = n\lambda,$$

is reflected onto a second crystal 4 again at the same glancing angle $\theta$ (namely 45°) and is reflected thereby towards detector means 5 which can comprise any convenient form of X-ray detector such as a gas ionisation chamber or a scintillation detector.

The first crystal 3 is fixedly mounted on a first member, diagrammatically represented by the straight line 7, pivotable as indicated by the arrows 6 relative to the source about a first axis 8 perpendicular to the plane of the spectrometer, i.e. the plane of the drawing. The second crystal 4 is fixedly mounted on a second member, represented diagrammatically by the line 11, which is pivotally carried by the first member 7 so as to be angularly displaceable relative to the first member 7 about a second axis 9 perpendicular to the plane of the spectrometer, as indicated by the arrows 12. The detector 5 is pivotally carried by the second member 11 so as to be angularly displaceable about a third axis 10 through the second crystal 4 and perpendicular to the plane of the spectrometer, as indicated by the arrows 13. The axes 8 and 10 are the same distance from the axis 9.

The spectrometer is provided with means not shown in FIG. 1 for adjusting the spectrometer wavelength $\lambda$. This is accomplished by changing the glancing angle $\theta$ of the first crystal 3 by an amount $\Delta\theta$, by displacing the first member 7 about the first axis 8 by that amount. In order to maintain the Bragg condition for reflection, the second member 11 is angularly displaced about the second axis 9 relative to the first member 7 by an amount $2\Delta\theta$, and the detector 5 is angularly displaced about the third axis 10 relative to the second member 11 by an amount $\Delta\theta$.

To this point the description could also be applied to spectrometer disclosed in U.S. Pat. No. 3,639,759, however in that disclosure the crystals are set parallel to the radii respectively joining the centre of each crystal to the second axis.

In a spectrometer in accordance with the invention each crystal 3, 4, is mounted on the corresponding first and second member 7, 11, so as to be respectively inclined in opposite directions through the same predetermined angle $\Phi$ to the direction joining the centre of the crystal to the second axis 9, wherein the value of $\Phi$ lies in the range from 50 to 70 degrees.

In the example illustrated by FIG. 1 the value of $\phi$ lies 60 degrees. It will be apparent that the angle $\psi$ between the radial lines 7 and 11 representing the first and second members is given by $$\psi = (180 - 2\phi) + 2\theta$$

and therefore, apart from the constant term $(180 - 2\phi)$, varies as $2\theta$ as the spectrometer wavelength is adjusted by adjusting $\theta$.

Figure 2:
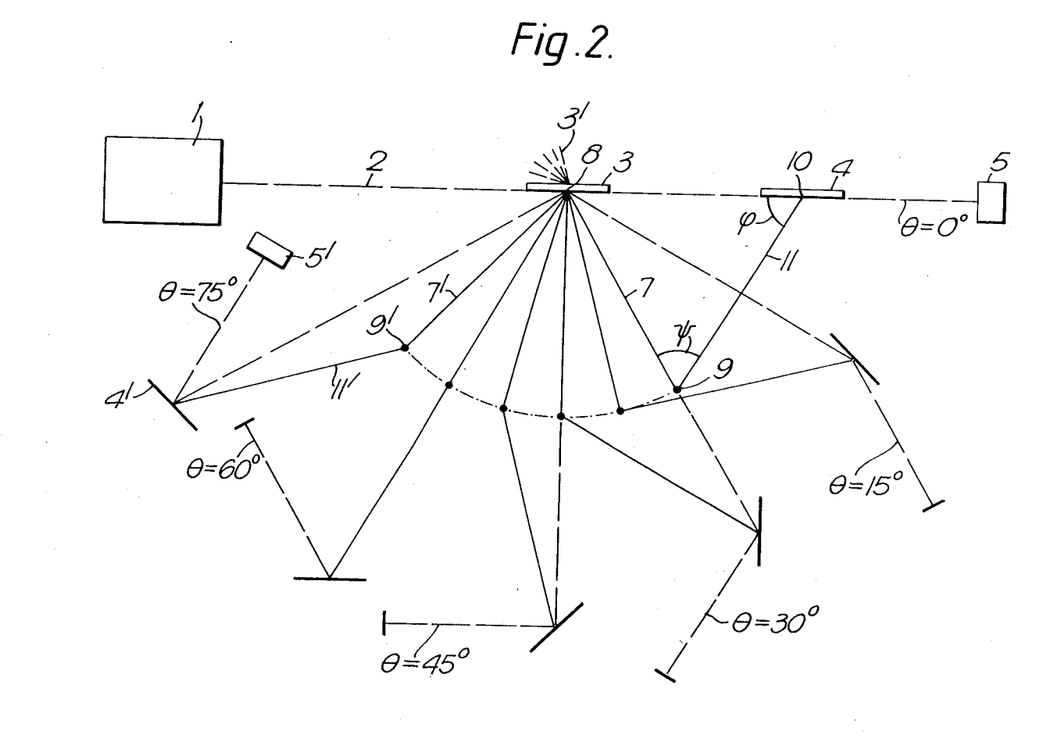
FIG. 2 is a schematic diagram illustrating the relative displacement of various components of FIG. 1 as the glancing angle and hence the wavelength is varied.

Successive configurations of the components of the spectrometer are indicated diagrammatically in FIG. 2 at intervals of 15° in the setting of the glancing angle $\theta$, from the technically non-useful value $\theta = 0°$ to a maximum value of $\theta = 75°$. The same reference numerals are used as in FIG. 1 for the first position ($\theta = 0°$) and the final positions are indicated by dashed reference numerals, the path taken by the second axis 9 is indicated by a dash-dot line.

Figure 3:
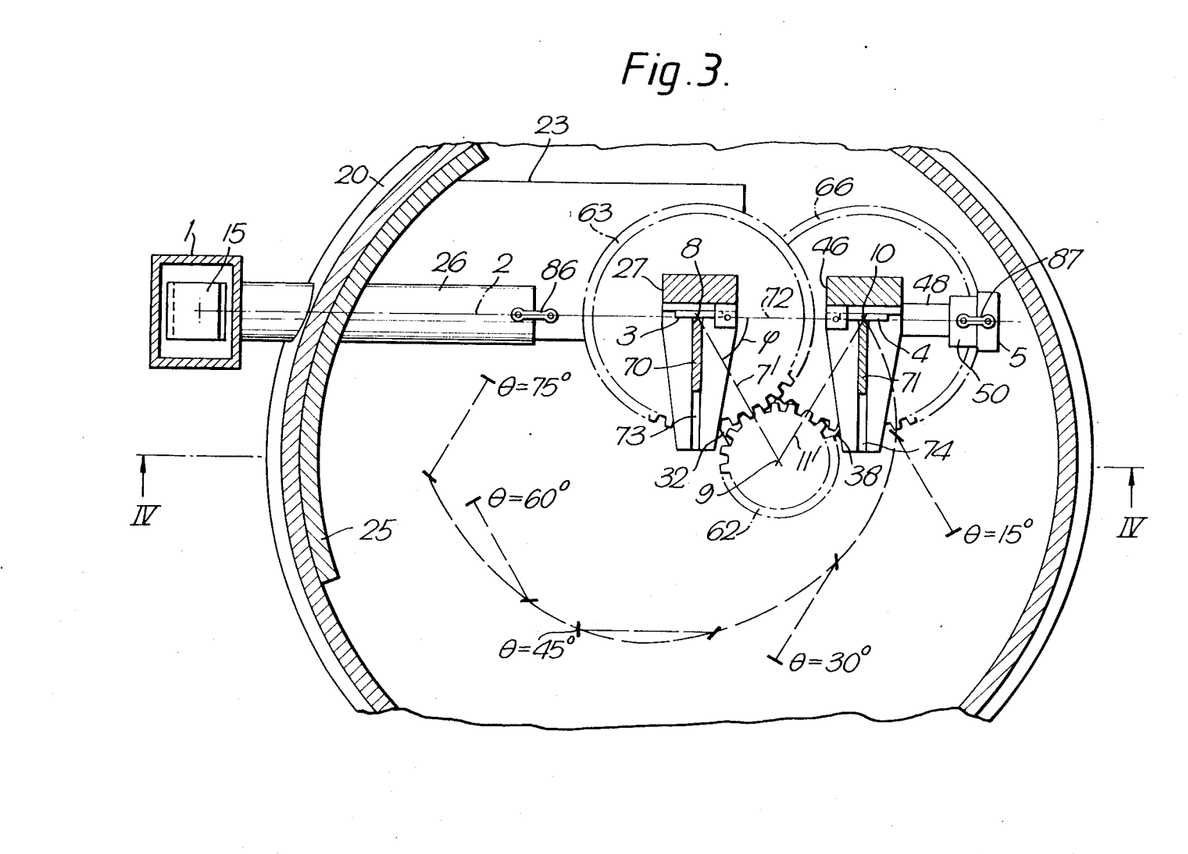
FIG. 3 is a plan view partly in section of an X-ray spectrometer in accordance with the invention.
Figure 4:
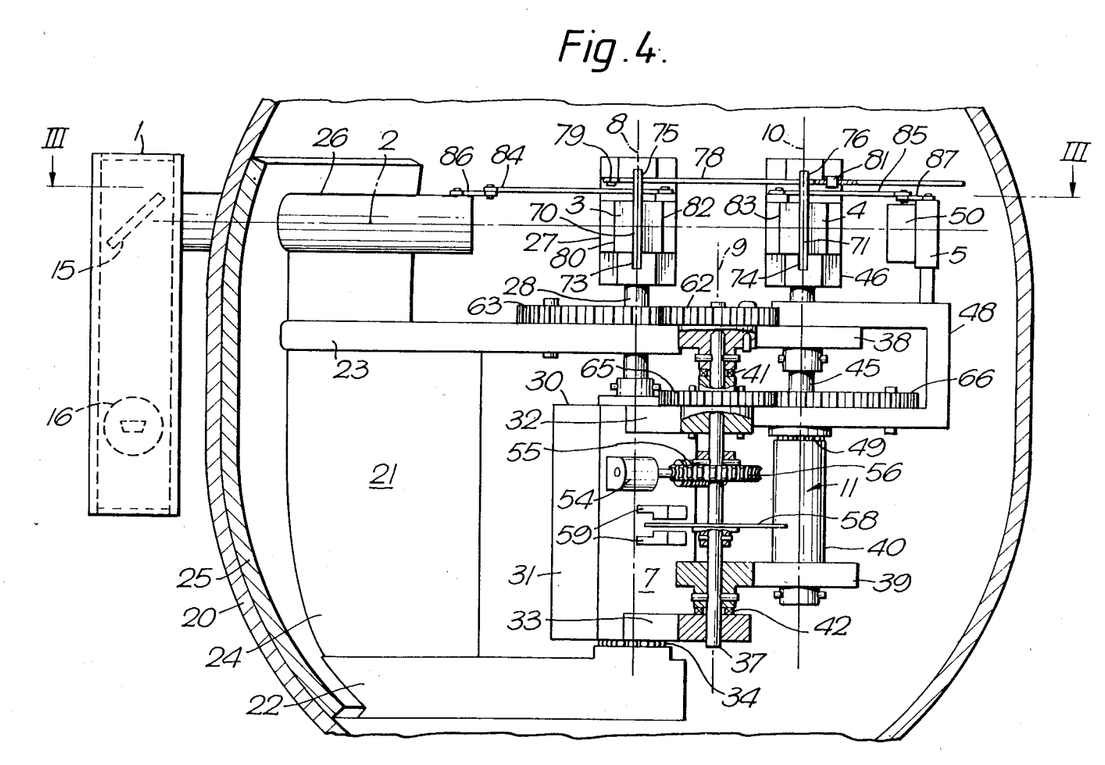
FIG. 4 is a frontal elevation partly in section of the apparatus of FIG. 3.

An embodiment of an X-ray spectrometer in accordance with the invention is illustrated schematically in plan view and in frontal elevation, both partly in section, in FIGS. 3 and 4, which represents the device set to a glancing angle $\theta = 0$ degrees for convenience of illustration, since it will be understood that the instrument is not used at $\theta = 0$, except, for alignment purposes.

A source 1 of X-radiation to be analysed, is fixedly attached to the body casing 20 of the spectrometer which comprises a cylindrical vacuum-tight chamber with hemispherical ends so that the spectrometer may be operated either in vacuo or in a helium atmosphere. When the spectrometer is used for its normal function of X-ray fluoroscopy, the source will comprise a sample substance under examination 15 mounted in a corresponding vacuum or helium filled space which communicates with the interior of the spectrometer casing via a mylar window (not shown), if desired, to prevent contamination of the analysing crystals. The sample 15 is irradiated with relatively hard X-rays from a conventional X-ray tube 16 either via a vacuum-tight beryllium window (not shown) or, if the tube 16 is included in the evacuated space, via a mylar window (not shown) to avoid contamination of the sample 15. The spectrometer can also be used to analyse primary X-radiation generated by a sample 15 under bombardment by an electron beam if desired. Source and sample arrangements for X-ray fluoroscopy are well known and will not be further described.

X-radiation to be analysed from the source 1, is passed into the spectrometer via a collimating cylindrical screen 26 which extends through an aperture in the casing 20 and forms a vacuum-tight seal with both the body casing 20 and the wall of the source assembly 1. The screen 26 is mounted on an upper platform 23 which latter together with a base 22 and a connecting support bar 24, form support means 21 for the spectrometer which is attached to the casing 20 by means of an attachment plate 25.

The X-radiation to be analysed is directed by the collimator 26 onto the first crystal 3 secured in a holder 27 fixedly mounted on a shaft 28 which is journalled in the base 22 and in the upper platform 23 so as to rotate about the first axis 8 through the crystal 3 and perpendicular to the plane of the spectrometer which in the present embodiment is horizontal.

Fixedly attached to the shaft 28 in the space between the base 22 and the upper platform 23 and supported by a thrust bearing 34, is a carrier 30 comprising a main support 31 through which the shaft 28 is passed and fixedly attached thereto, and upper and lower supporting arms 32, 33, respectively. The carrier 30, the shaft 28 and the crystal holder 27 together form the first member 7 shown in FIGS. 1 and 2.

A further shaft 37 is journalled at the outer extremities of the arms 32, 33, so as to be rotatable about a vertical axis corresponding to the second axis 9 of FIGS. 1 and 2. The shaft 37 is fixedly attached to upper and lower arms 38 and 39 which together with a cylindrical bearing support pillar 40 and a shaft 45 form the second member 11, shown in FIGS. 1 and 2, which is pivotally carried by the first member 7 via thrust bearings 41, 42.

The shaft 45 is fixedly attached to the far ends of the upper and lower arms 38, 39. The second crystal 4, secured in a holder 46, is fixedly mounted on the upper end of the shaft 45 so as to receive X-radiation reflected from the first crystal 3. The crystals 3 and 4 are equidistant from the shaft 37 representing the axis 9. The shaft 45 serves as a bearing about which a detector support 48 can rotate supported on a thrust bearing 49. The detector 5 is mounted on the support 48 so as to receive X-radiation reflected from the second crystal 4 via an input shield 50 which provides a screened radiation passage of rectangular cross section.

The wavelength to which the spectrometer is set, is controlled by a drive motor 54, conveniently a direct current motor with suitable control circuitry (not shown), which can be of conventional form, and is mounted on the main support 31 of the first member 7. The output shaft of the motor 54 is provided with a worm gear 55 which meshes with the toothed periphery of a gear wheel 56 fixedly attached to the shaft 37 forming part of the second member 11. The angle $\psi$ (see FIG. 1) between the first and second members 7 and 11, is measured by means of a graticule disc 58 and associated optical sensing head 59 arranged conventionally to provide direction sensitive count pulses to a bidirectional counter (not shown) which is arranged to provide an indication of the angle $\psi$, and hence of the spectrometer wavelength in conjunction with the crystal constants.

A gear wheel 62 is mounted on the top of the shaft 37 and is fixedly attached to the upper arm 38 of the second member 11. A further gear wheel 63 centred about the first axis 8, is fixedly attached to the upper platform 23. The gear wheel 63 meshes with the gear wheel 62 and has a diameter twice that of the latter. Thus, operation of the motor 54 to cause a change $\Delta\psi$ in the angle $\psi$ between the first and second members 7 and 11, will cause the gear wheel 62 to displace the first member 11 which carries the first crystal 3 about the axis 8 so as to cause a change $\Delta\theta$ in the glancing angle $\theta$ (FIG. 1), which will equal $\Delta\psi/2$.

A further small gear wheel 65 is rotatably mounted on the shaft 37 and fixedly attached to the upper supporting arm 32 of the first member 7. A further large gear wheel 66 is arranged to be rotatable about the shaft 45 centred on the third axis 10, and is fixedly attached to the detector support 48. The gear wheel 66 meshes with the gear wheel 65 and has a diameter twice that of the latter. Thus operation of the motor 54 to cause a change $\Delta\psi$ in the angle $\psi$ between members 7 and 11 will cause the gear wheel 66 to displace the detector support 48 and hence the detector 5 about the axis 10 so as to cause a corresponding change $\Delta\theta$ in the direction of the axis of the detector relative to the orientation of the second crystal 4.

In accordance with the invention the first and second crystals 3, 4, are mounted on the corresponding first and second members 7, 11, so as to be respectively inclined in opposite directions through the same predetermined angle $\Phi$ to the corresponding straight line direction 7', 11', joining the centre of the respective crystal 3, 4, to the second axis 9 wherein the value of $\Phi$ lies in the range from 50 to 70 degrees, and in the present embodiment $\phi = 60$ degrees.

Figure 5:
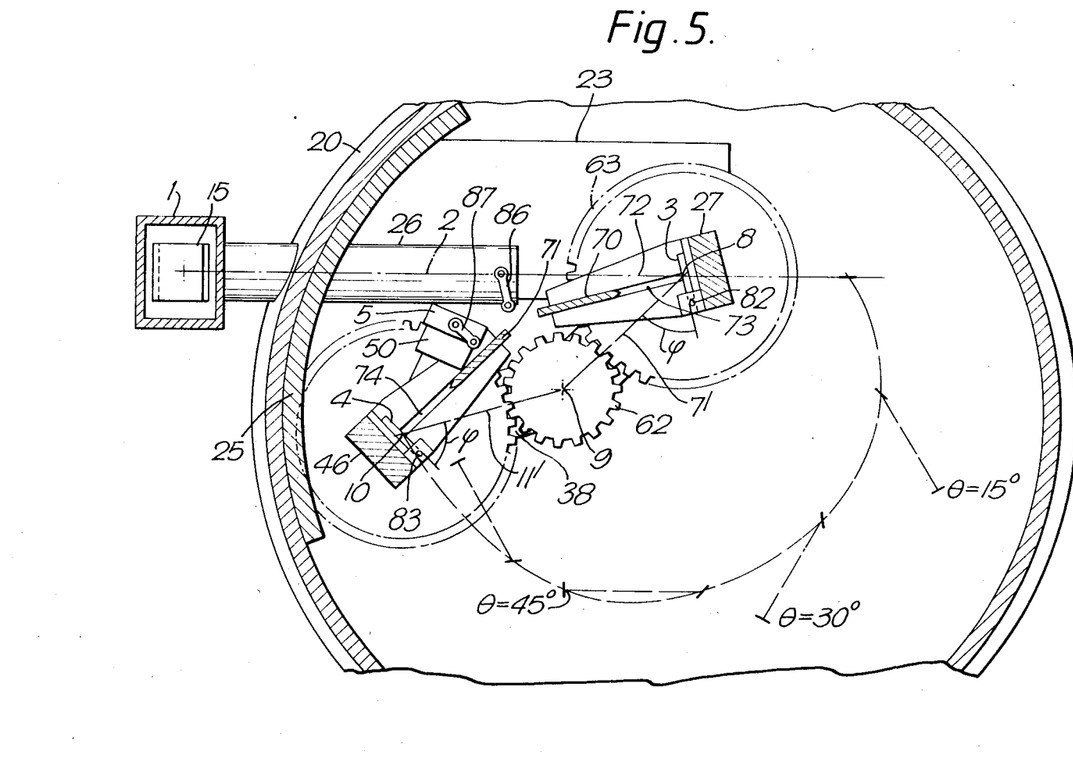
FIG. 5 is a plan view of the apparatus of FIG. 3 set to the maximum glancing angle.

An advantage of this arrangement will be apparent from FIG. 5 which shows the disposition of the parts of the spectrometer when set to a glancing angle $\theta = 75$ degrees. The intermediate positions of the second crystal 4 and of the detector 5 are indicated as in FIG. 2 and it will be seen that the spectrophotometer can readily be adjusted over a range of $\theta$ from just above zero to as much as 75 degrees with the minimum of difficulty, a range of adjustment that was not possible with the prior arrangement.

In accordance with a feature of the invention, respective first and second screening blades 70, 71, are provided, and each are arranged so as to be respectively displaceable in a direction perpendicular to the associated reflecting plane of the corresponding first and second crystal 3, 4, along a path 73, 74 which passes through the corresponding first and second axis 8, 10. Displacement means are arranged to displace the screening blades 70, 71, in response to an adjustment of the spectrometer wavelength so that the edge of each screening blade nearest the crystal, is maintained just clear of the path of that part of the spectrometer beam which can pass from the source 1 to the detector 5 via Bragg reflection in the first crystal 3 and then in the second crystal 4.

In the embodiment, the displacement means comprises a system of linkages 78, 84, 85, 86 and 87 disposed outside the path of the spectrometer beam, in the form of levers coupled to respond to the attitudes of the first and second crystals 3, 4, relative to the direction of incidence of the spectrometer beam. One of said linkages comprises a single elongate member in the form of a rod 78 attached at one end by a pivot 79 to an overhang on the crystal holder 27 forming part of the first member 7 at a point corresponding to the upward projection perpendicular to the plane of the spectrometer, of the front edge 80 of the first crystal 3. The other end of the rod 78 is similarly pivotally attached to an overhang on the crystal holder 46 forming part of the second member 11 by means of a pivotal sleeve 81 which is slidable longitudinally along the rod 78.

The other said linkages comprise two parallelogram linkages. A first said linkage comprising a rod 84 and a linking member 86 pivotally mutually attached at one end, and the second linkage similarly comprising a rod 85 and a linking member 87. The other end of the linking member 86 is pivotally connected to the support means 21 at the top of the collimating cylindrical screen 26, and the other end of the linking member 87 is pivotally connected to the top of the housing of the detector 5, both pivotal points lying on a vertical upward projection of the central axis 72 of the spectrometer beam. The other ends of the respective rods 84 and 85 are pivotally connected, respectively, to the first and second members 7 and 11 at points near the top of the crystal holders 27 and 46 corresponding to the vertical upward projections of the adjacent edges 82 and 83 of the first and second crystals 3 and 4. This arrangement ensures that each rod, 84 and 85, is maintained parallel to the corresponding edge of the spectrometer beam, and this can be seen from FIGS. 6 and 7 which illustrate the operation of the linkages as the glancing angle $\theta$ is set to 30 degrees (FIG. 6) and to 60 degrees (FIG. 7).

Figure 6:
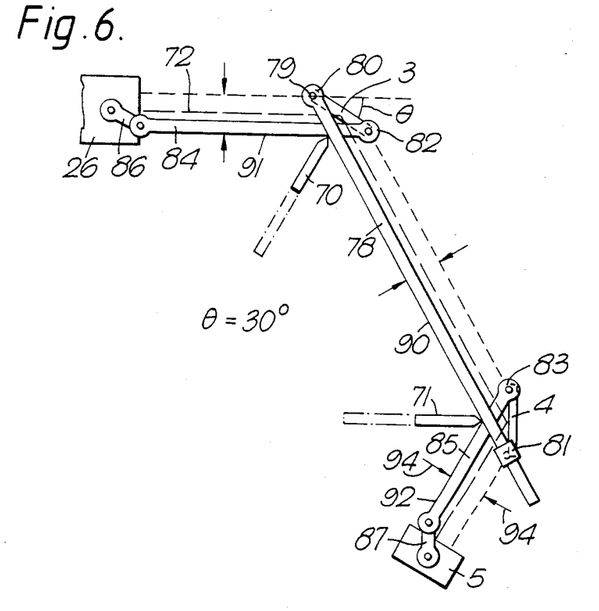
FIGS. 6 and 7 are diagrams illustrating the X-ray shield operating linkages for the apparatus of FIG. 3 for a small and a large glancing angle, respectively.
Figure 7:
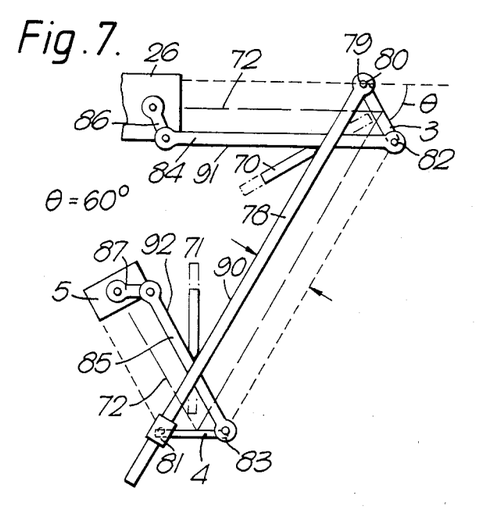

It will be seen from FIG. 4 that the rod 78 is located above the rods 84 and 85, and from FIGS. 6 and 7, that the rod 78 overlaps the rod 84 directly in front of the first crystal 3, and also overlaps the rod 85 directly in front of the second crystal 4. The scissors action thereby provided is employed to displace the corresponding screening blade 70 and 71 along associated upper and lower tracks 75, 73 and 76, 74 in the respective crystal holders 27 and 46 against the action of corresponding springs (not shown) which are arranged in a conventional manner to urge the blades into contact with the corresponding pairs of rods.

The straight edge 90, 91 and 92 of each of the rods 78, 84 and 85 which contacts the screening blade 70 or 71, is set back so that it almost coincides with the line joining the axes of the pivot at each end of the rod. Because the pivots at the crystal end of the rods are located above the corresponding edge of the respective crystal and the rods 84 and 85 form part of parallelogram linkages, the edges 91, 90 and 92 lie just clear of the corresponding boundary of that part of the spectrometer beam, indicated by the arrows 94, which can pass from the source 1 to the detector 5 via the process of Bragg reflection in the first and second crystals 3, 4. Consequently, the edge of the respective screening blade 70, 71 bearing on the corresponding intersecting edges 91, 90 and 90, 92 will be maintained just clear of said part of the spectrometer beam as the spectrometer wavelength is varied by means of the motor 54.

The blade 70 and 71 are made of a heavy metal so as to provide sufficient screening of unwanted scattered X-radiation (background) and can be made, for example, of molybdenum or of lead supported on sheet steel.

The provision of the screening blades 70, 71, makes it unnecessary to use conventional vertically disposed Soller slits to prevent scattered radiation from entering the detector 5. However, the resolution provided by the double crystal X-ray spectrometer can be so high that it may be desirable to provide horizontal Soller slits at the input end of the beam path to ensure that the detected radiation can only be received via a path which is accurately parallel to the plane of the spectrometer. This is because the Bragg condition for X-radiation travelling at an angle greater than about 1 degree to the spectrometer plane may be sufficiently different from that of coplanar radiation to degrade the attainable resolution.

It will be apparent that it may be difficult to rely solely on the scissors effect to displace the blades 70, 71 when use is to be made of the higher values of $\theta$. Alternative methods of displacing the blades can be provided which employ a simple servo with means for sensing either the corresponding edge of rods or of using the spectrometer angle information supplied by the sensing head 59 together with a look up table for corresponding positions for the blades. For a more restricted range of values for $\theta$, say up to $\theta = 60$ degrees, the need for the full scissors action of the rods 84, 78 and 78, 85 can be avoided if the blades 70, 71 are adequately supported against the resultant side thrust, by only using the rod 78 or only using the parallel linkages 84, 86 and 85, 87, since along the paths 73 and 74 the corresponding edges 91 and 90 or 90 and 92 will occupy the same position for the same value of $\theta$. Again, if it is not desired to drive the blades directly with the linkage rods, a simple servo system with an edge sensor can be employed over the full range of $\theta$.

By mounting the screening blades 70, 71, in front of the respective crystals 3, 4, in the manner described, the spectrometer can be made more compact as compared with prior arrangements in which a Soller slit was used to screen the detector from scattered radiation. The resultant reduction in overall size for the same size of crystal can provide significant savings in the cost of providing the vacuum-tight casing 20 for the spectrometer.

What is claimed is:

1. A two-crystal X-ray spectrometer including support means fixed relative to a source of X-radiation to be analysed, a first crystal fixedly mounted on a first member pivotable relative to said support means about a first axis through the first crystal and perpendicular to the plane of the spectrometer, a second crystal fixedly mounted on a second member pivotally carried by said first member so as to be angularly displaceable about a second axis perpendicular to the plane of the spectrometer, said first and second crystals being spaced from said second axis by the same distance, detector means pivotable about a third axis through the second crystal and perpendicular to the plane of the spectrometer, the source, the first and second crystals and the detector means being arranged relative to one another such that when X-radiation corresponding to the wavelength to which the spectrometer is adjusted, is directed from the source onto the first crystal, it will be reflected in accordance with the Bragg condition for reflection onto the second crystal and, similarly, from thence onto the detector means, and means for adjusting the spectrometer wavelength comprising angular displacement means for respectively displacing the first member about the first axis and the detector means relative to the second member about the third axis, each by an angular amount $\Delta\theta$, and for displacing the second member about the second axis relative to the first member by an angular amount $2\Delta\theta$, characterized in that each crystal is mounted on the corresponding first and second member so as to be respectively inclined in opposite directions through the same predetermined angle $\Phi$ to the direction joining the centre of the crystal to the second axis, wherein the value of $\Phi$ lies in the range from 50 to 70 degrees.

2. An X-ray spectrometer as claimed in claim 1, characterised in that there are provided respective first and second screening blades each arranged to be respectively displaceable in a direction perpendicular to the associated reflection plane of the corresponding first and second crystal along a path which passes through the corresponding first or third axis, and means arranged to displace the screening blades in response to a said adjustment of the spectrometer wavelength so that the edge of each screening blade is maintained just clear of the path of that part of the spectrometer beam which can pass from the source to the detector via Bragg reflection in the first and second crystals.

3. An X-ray spectrometer as claimed in claim 2, characterised in that said first and second screening blades are arranged to be slidable along a corresponding track and are mechanically displaceable by means of a linkage disposed outside the path of the spectrometer beam, comprising at least one lever coupled to respond to the attitudes of said first and second crystals relative to the direction of incidence of the spectrometer beam.

4. An X-ray spectrometer as claimed in claim 3, characterised in that said linkage comprises a single elongate member pivotally attached at one end to said first member at a point corresponding to the projection perpendicular to the plane of the spectrometer of the front edge of the first crystal relative to the direction of propagation of the spectrometer beam, the other end being pivotally attached to said second member at a point similarly corresponding to the projection of the furthest edge of the second crystal, one of the pivotal attachments being slidable longitudinally along said elongate member, said elongate member being slidably connected to each said screening blade so as to displace said blade along the corresponding track in response to a said adjustment of the spectrometer wavelength.

5. An X-ray spectrometer as claimed in claim 3 or claim 4, characterized in that said linkage comprises a first and a second parallelogram linkage, each comprising a rod and a linking member pivotally mutually attached at one end, the other ends of the respective rods being pivotally connected, respectively, to said first and said second members at points corresponding to the respective projections thereon perpendicular to the plane of the spectrometer, of the adjacent edges of said first and second crystals, and the other ends of the linking members being respectively pivotally connected to said support means and to said detector on the respective projection perpendicular to the plane of the spectrometer of the central axis of the corresponding portion of the spectrometer beam respectively directed towards said first crystal and reflected from said second crystal, the arrangement being such that each rod is maintained parallel to the corresponding edge of the spectrometer beam and is slidably connected to a corresponding screening blade thereby to displace said blade along the corresponding track in response to a said adjustment of the spectrometer wavelength.

6. An X-ray spectrometer as claimed in claim 5, characterised in that said screening blades are each spring loaded in a direction towards the corresponding crystal and said elongate member and a corresponding rod from said parallelogram linkages are arranged respectively and partially to overlap in a scissor-like manner so as to receive the front edge of the corresponding screening blade thereby to displace said blade in opposition to said spring loading in response to a said adjustment of the spectrometer wavelength.

* * * * *